United States Patent [19]
Thomas et al.

[11] Patent Number: 5,166,177
[45] Date of Patent: Nov. 24, 1992

[54] METHOD FOR REPELLING INSECTS

[75] Inventors: James J. Thomas, Rocky Ridge; Baron L. Tayler, Sabillasville, both of Md.

[73] Assignee: Journeys End International, Inc., Denver, Pa.

[21] Appl. No.: 533,403

[22] Filed: Jun. 5, 1990

[51] Int. Cl.$^5$ .............................................. A01N 37/02
[52] U.S. Cl. .................................... 514/557; 514/492; 514/494; 514/499; 514/502; 514/724; 514/919; 424/DIG. 10
[58] Field of Search ............... 514/494, 499, 502, 557, 514/724, 492, 919; 424/DIG. 10; 426/74, 648

[56] References Cited

U.S. PATENT DOCUMENTS 4,507,291 3/1985 Smolanoff ............................ 514/278
4,663,346 5/1987 Coulston et al. ..................... 514/456

*Primary Examiner*—Carolyn Elmore
*Assistant Examiner*—John D. Pak

[57] ABSTRACT

The present invention relates to a method for imparting insect repelling qualities to the hide or skin of animals by orally administering small but effective amounts of acetate salts to the animals, preferably on a daily basis.

9 Claims, No Drawings

METHOD FOR REPELLING INSECTS

BACKGROUND OF THE INVENTION

The invention relates to a method for effectively repelling biting insects from the skins or hides of animals by orally administering to the animals certain acetate salts.

The control of insects, particularly biting or burrowing insects such as stable flies, other types of flies, ticks, mosquitos, gnats, lice, chiggers, mites and the like, is a particularly important problem for both humans and domestic animals including horses, sheep, dogs, and cats. Particular concern is currently being directed to possible method of control for diseases, such as Rocky Mountain Spotted Fever and Lyme Disease that are transmitted by ticks. Previous methods of repelling insects primarily centered on topical solutions or sprays that were necessarily applied over the whole body surface of the animal. Vinegar or tobacco juice have been added to feed for horses, in an attempt to diminish the fly population around horses.

SUMMARY OF THE INVENTION

Accordingly, it is an object of the present invention to orally administer a composition to animals to provide the skin or hide of the animals with insect repelling qualities.

It is a further object of the present invention to provide an orally administered composition to impart insect repelling qualities to the skin or hide of animals wherein the composition can be co-administered with food without deleteriously effecting the flavor or odor characteristics of the food.

The present invention relates to a method for imparting insect repelling qualities to the hide or skin of animals by orally administering small but effective amounts of acetate salts to the animals, preferably on a daily basis

DETAILED DESCRIPTION OF THE INVENTION

It has been determined that the oral administration to animals including humans of acetate salts (salts of acetic acid) provides the skins or hides of animals with insect repellent qualities. These insect repelling qualities include the repelling of biting flies and other insects, including gnats, ticks and the like from the skin or hide of the animals.

Any non-toxic acetate salt that dissociates in the stomach of an animal can be utilized in accordance with the method of the present invention. Preferred acetate salts for use in the present invention include, but are not limited to: alkali metal acetates, most preferably sodium acetate and potassium acetate; and alkaline earth metal acetates, preferably calcium acetate or magnesium acetate. Any other non-toxic metallic acetate salts, including but not limited to, zinc acetate and ferric acetate can also be employed. Naturally, toxic metal salts such as lead acetate should not be employed. Mixtures of various acetate salts are also considered to be within the scope of the present invention.

The acetate salts utilized in the method of instant invention are orally administered to the animals, including humans, in a minimum dosage of 0.30 grams per 100 pounds of body weight of the animal to provide daily protection by imparting insect repellency to the skin or hide of the animal The maximum dosage of the acetate salts are non-toxic amounts which may vary with the specific salt. The preferred dosage regimen comprises oral administration of an active but non-toxic quantity in a dosage range from about 0.5 to about 4.0 grams per 100 pounds of body weight of the animal, most preferably from about 0.75 to about 1.5 grams. Precise optimum dosages are dependent upon the species of animal and the weight of the subject and can be determined by those skilled in the art.

The present composition or preparation for oral administration can include, for example, a tablet, capsule, powder, granule or fine granule form. These dosage forms may be easily prepared according to conventional technique and may comprise commonly employed excipients, binding agents, disintegrators, glidants and other pharmaceutical agents. As the excipient, binding agent and/or disintegrator, there may be, for example, microcrystalline cellulose, wheat starch, sugar, lactose, gum arabic, tragacanth gum, carboxymethyl-cellulose and so on. As the glidant, there may be used, e.g., magnesium stearate and talc. Tablets may be also coated according to conventional coating procedures and any commonly employable coating materials such as, for example, shellac, ethylcellulose, hydroxymethyl-cellulose, polyvinyl pyrrolidone, titanium dioxide and the like may be favourably applied for such purposes. It is further recognized that the instant composition may be formulated to be time released to prolong the insect repellent effect upon the animal imbibing the acetate salt composition. Such time release formulations are easily formulated by those skilled in the art.

The instant acetate salts may be administered directly or may be mixed and co-administered with food or animal feed. The co-administration of the acetate salts with food has no deleterious organoleptic effects upon the taste of the feed while maintaining the efficacy of the insect repelling qualities of the acetate salt after ingestion. The acetate salts of the present invention can also be dissolved and administered in water.

The oral administration of the above-described acetate salts to animals, including humans, provides the skin or hide of the animals with aromatic, insect repelling qualities through their sweat to repel common insect pests such as flies, mosquitos, ticks, fleas, lice, mites and the like. Typically, the administration of efficacious amounts of the acetate salts to animals provides the skin or hide of larger animals such as horses with prolonged insect repelling qualities after about two weeks of daily dosages. Subsequent continuous daily dosages provide the animals with insect repelling qualities lasting approximately up to twenty-four hours per dose depending upon the climate and species of animal. Smaller animals, such as dogs and cats, may require higher dosages due to their higher metabolic rates and may exhibit aromatic, insect repelling qualities for prolonged periods after a few days from the initial daily dosage regimen of an acetate salt.

The oral administration of the acetate salts of the present invention to a host, including humans, provides the host with repellency against insects such as ticks from burrowing into and infecting the host with transmittable diseases such as Rocky Mountain Spotted Fever or Lyme Disease The instant method could be utilized by incorporating acetate salts into salt lick blocks for administration in suitable dosages.

The following examples are intended to illustrate the invention but not to limit the scope thereof.

EXAMPLE 1

Three horses, weighing approximately 1000 lbs. each, were each fed daily dosages of approximately 20 grams of sodium acetate in powder form by the addition of the powdered sodium acetate to horse feed for three weeks. After two weeks, flies noticeably avoided the horses for the full 24 hour periods between dosage administration. At the end of three weeks, the horses were checked and no ticks were discovered. The skin of the horses revealed scabs where dozens of ticks had apparently previously been located but had dropped off with only healing bite wounds remaining.

I claim:

1. A method of repelling ticks from the hide or skin of non-human animals comprising orally administering to said animals a tick repelling amount of a non-toxic alkali metal or alkaline earth metal acetate salt.

2. The method of claim 1 wherein said salt is an alkali metal acetate.

3. The method of claim 2 wherein said alkali metal acetate is sodium acetate.

4. The method of claim 1 wherein said salt is an alkaline earth metal acetate.

5. The method of claim 1 wherein said insect repelling amount comprises between at least 0.30 grams and a non-toxic amount of said repelling composition per 100 pounds of animal body weight.

6. The method of claim 5 wherein said repelling amount is administered daily.

7. The method of claim 1 wherein said repelling amount is mixed with animal feed prior to administration.

8. The method of claim 1 wherein said insect repelling amount comprises from about 0.5 to about 4.0 grams of said repelling composition per 100 pounds of animal body weight.

9. The method of claim 1 wherein said salt is selected from the group consisting of sodium acetate, potassium acetate, calcium acetate, magnesium acetate, or mixtures thereof.

* * * * *